United States Patent [19]

Arpe

[11] 4,324,921

[45] Apr. 13, 1982

[54] PROCESS FOR THE MANUFACTURE OF ETHERS OF HYDROXY-PIVALALDEHYDE

[75] Inventor: Hans-Jürgen Arpe, Frankfurt am Main, Fed. Rep. of Germany

[73] Assignee: Hoechst Aktiengesellschaft, Frankfurt am Main, Fed. Rep. of Germany

[21] Appl. No.: 154,319

[22] Filed: May 29, 1980

[30] Foreign Application Priority Data

Jun. 2, 1979 [DE] Fed. Rep. of Germany ....... 2922698

[51] Int. Cl.$^3$ ...................... C07C 45/60; C07C 47/19
[52] U.S. Cl. ................................... 568/427; 568/443; 568/450; 260/340.7
[58] Field of Search ............... 568/450, 486, 427, 483, 568/483, 443

[56] References Cited

U.S. PATENT DOCUMENTS 3,676,500  7/1972  Montell et al. ................ 568/450 X

OTHER PUBLICATIONS

Rondestvedt et al., JACS, vol. 82 (1960), pp. 6419–6420.
Rondestvedt et al., JACS, vol. 84 (1962), pp. 3307–3319.

*Primary Examiner*—Bernard Helfin
*Attorney, Agent, or Firm*—Curtis, Morris & Safford

[57] ABSTRACT

Ethers of the hydroxypivalaldehyde $RCH_2OCH_2C(CH_3)_2CHO$ are prepared by a catalytic isomerization of 5,5-dimethyl-1,3-dioxans at 250° to 500° C. The catalyst is obtained by way of calcination from silicon dioxide, at least one element of the third main group or subgroup in the form of its oxide or hydroxide and at least one alkali metal oxide or hydroxide.

3 Claims, No Drawings

PROCESS FOR THE MANUFACTURE OF ETHERS OF HYDROXY-PIVALALDEHYDE

The subject of the present invention is a catalytic process for the manufacture of ethers of hydroxypivalaldehyde of the formula $RCH_2OCH_2$—$C(CH_3)_2CHO$ by the isomerization of 5,5-dimethyl-1,3-dioxans.

Hydroxypivalaldehyde or 2,2-dimethyl-3-hydroxypropanal(1), $HOCH_2$—$C(CH_3)_2CHO$ may be obtained in a simple and economical manner from formaldehyde and isobutyraldehyde by an aldol reaction (Chemiker Ztg. 97, 53 (1973)). However, the two functional groups lead to an intermolecular reaction, so that the hydroxypivalaldehyde is present as a bimolecular hemiacetal with a 1,3-dioxan structure:

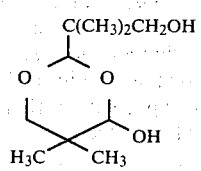

In this compound the aldehyde group of the hydroxypivalaldehyde is largely masked, so that many characteristic aldehyde reactions are made difficult, for example the oxidation to give carboxylic acid or the reaction to yield an oxime. Some reactions can no longer be carried out at all, for example the reaction with dinitrophenyl hydrazine.

Compared against the hydroxypivalaldehyde itself, its ethers have the considerable advantage that the aldehyde group is available for various reactions, since the blocked hydroxyl group can no longer effect an internal aldol formation.

However, a normal etherification of the hydroxyl group in the hydroxypivalaldehyde by reaction with an alcohol is rather difficult. For example, the ether synthesis according to Williamson is performed via the alkali metal alcoholate of hydroxypivalaldehyde, and due to the alkaline conditions required in this process, various side-reactions are involved, especially condensation reactions.

Yet for some time there has been known a novel catalytic isomerization reaction of 5,5-dimethyl-1,3-dioxan itself or the derivatives thereof which are substituted in the 2-position, which reaction yields ethers of hydroxypivalaldehyde (J. Amer. Chem. Soc. 82, 6419 (1960)):

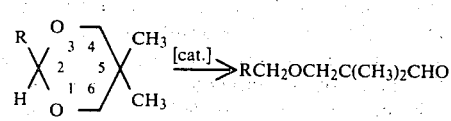

The 5,5-dimethyl-1,3-dioxans serving as starting material in this reaction may—as derivatives of neopentyl glycol—be obtained in a very easy manner and a good yield by a proton catalyzed reaction of neopentyl glycol with aldehydes:

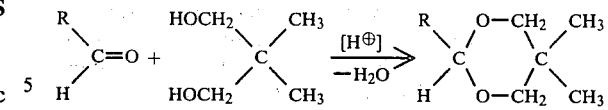

In the simplest case R is hydrogen, i.e. the starting material is formaldehyde which leads to the methyl ether of hydroxypivalaldehyde via 5,5-dimethyl-1,3-dioxan. Thus, the aldehyde group of the starting aldehyde yields a $CH_2$ group in the ether of hydroxypivalaldehyde.

This isomerization reaction has been examined to a very large extent with regard to its mechanism and action of catalysts (J.Amer.Chem.Soc. 84, 3307 (1962)) and it was found that acidic catalysts are required for an isomerization and that of a great number of substances tested only silica gel and aluminum silicate in the form of pumice may practically be used as catalysts. But the activity and selectivity of these catalysts are not yet satisfactory from the economical point of view. Thus, the benzyl ether of hydroxypivalaldehyde can be prepared in the most favorable case with pumice with a conversion of 90 molar % and a selectivity of 83.3 molar %, i.e. a yield of 75 molar %. For the 2-methylpropyl ether, the yield with the same catalyst is 69 molar %, with a conversion of 84 molar % and a selectivity of 82.1 molar %, whereas the methyl ether is formed only in a yield of 38 molar %. When $SiO_2$ is used as catalyst instead of pumice, the yield of the benzyl ether is even markedly lower, i.e. 46 molar %.

Besides, it has become evident that the activity of pumice is rapidly reduced—apparently depending on various impurities—, so that either a regeneration or a frequent change of the catalyst is required.

The insufficient specification of the natural product pumice, whose composition may vary depending on its origin, may easily involve uncontrollable influences on the reaction (Houben Weyl, Methoden der Org. Chemie IV, 2, page 149 (1955)).

It has therefore been the object of this invention for the manufacture of ethers of hydroxypivalaldehyde by the isomerization of 5,5-dimethyl-1,3-dioxans to provide a catalyst being active and selective for a prolonged period of time which shows a well-defined and thus reproducible composition.

The subject of the present invention is therefore a process for the manufacture of ethers of hydroxypivalaldehyde of the formula $RCH_2OCH_2$—$C(CH_3)_2CHO$ by the isomerization of 5,5-dimethyl-1,3-dioxans, which comprises carrying out the isomerization with 250° to 500° C. at a catalyst which is formed of
a. silicon dioxide
b. at least one element of the third main group or subgroup in the form of the oxide or hydroxide
c. at least one alkali metal oxide or hydroxide
by calcination at 600° to 1000° C. for 30 minutes to 8 hours.

It is a surprising fact that it is necessary notwithstanding to the teaching provided by the discoverers of the isomerization reaction, according to which acidic catalysts such as silica gel or aluminum silicates are particularly suitable, to block the acidic effect of $SiO_2$ or of silicates or calcined mixtures of $SiO_2$ and the oxides or hydroxides of the metals of the third main group and/or subgroup by adding alkali metal oxides or hydroxides, in order to obtain a high activity and selectivity The radical R in the formula RCH$_2$OCH$_2$—C(CH$_3$)$_2$-CHO of the ethers of hydroxypivalaldehyde prepared according to the invention may be hydrogen, a linear or branched alkyl radical with from 1 to 17 carbon atoms, a cycloalkyl radical with from 5 to 12 carbon atoms or an aryl radical which may also be substituted by alkyl, alkoxy or halogen radicals.

R represents preferably hydrogen, linear or branched alkyl of from 1 to 12 carbon atoms, one of the three cycloalkyl radicals —C$_6$H$_{11}$, —C$_{10}$H$_{19}$, —C$_{12}$H$_{23}$, or the unsubstituted or methyl-substituted phenyl radical.

Yet it is even more preferred if R is hydrogen, linear or branched alkyl of from 1 to 7 carbon atoms, cyclohexyl or phenyl.

As metals of the third main group or subgroup in the form of their oxides or hydroxides there may be mentioned above all Al, Ga, In, La and the rare earths, i.e. the lanthanides of the periodic numbers 58 to 71, i.e. from cerium to lutetium inclusive. The rare earths may be employed individually, for example cerium, or as mixtures, as they are common in commerce as "didymium" (Di=didymium consists in most cases of a mixture of lanthanum, cerium, praseodymium, neodymium, as well as small amounts of samarium, gadolinium, ytterbium, and others). Particularly preferred are the oxides or hydroxides of aluminum and/or of didymium.

The amount of the metals of the third main group or subgroup (abbreviated as Me$^{III}$ in the following) may vary within wide limits; generally it is in the range of from 1 to 100 mmols (calculated as Me$_2^{III}$O$_3$), preferably from 4 to 40 mmols, per 100 g of SiO$_2$.

As alkali metals (abbreviated as Me$^I$ in the following), which are present generally in the form of their oxides or hydroxides on the system consisting of SiO$_2$ and the oxides or hydroxides of the metals of the third main group or subgroup, there may be used Li, Na, K, Rb or Cs. Preference is given to sodium and/or potassium. Their amount is generally in the range of from 1 to 200 mmols (calculated as Me$_2^I$O), preferably from 10 to 100 mmols, per 100 g of SiO$_2$.

The mixture of SiO$_2$ and the oxides or hydroxides of the metals of the third main group or subgroup is prepared in accordance with common methods. Thus, it is possible, for example, to jointly precipitate the oxides or hydroxides from water-soluble salts of the above-mentioned metals and water-soluble alkali metal silicates, by adding alkali metal hydroxide. Alternatively, SiO$_2$ may be impregnated in the form of kieselguhr or silica gel of an appropriate pore structure with aqueous solutions of inorganic salts of the metals of the third main group or subgroup, such as the chlorides, nitrates, sulfates, or organic salts, such as acetates, and these metal compounds may be precipitated on the SiO$_2$ by an alkaline treatment or by thermolysis into the oxides or oxide hydrates.

The precatalyst thus obtained is carefully washed until the water no longer contains ions and is then impregnated with an alkali metal compound, such as the alkali metal oxide, hydroxide, hydrogenocarbonate, carbonate or carboxylate (for example alkali metal acetate). In the course of the calcination as described below the alkali metal compounds are also converted generally into the oxides or hydroxides.

In order to obtain a catalyst which is as active and selective as possible, it is necessary according to the invention to subject the precatalyst consisting of the oxides or hydroxides of the above-mentioned metals to a calcination in the temperature range of from 600° to 1000° C. for a period of from 30 minutes to 8 hours, preferably at 850° to 950° C. for 1 to 3 hours.

It was a surprising fact that the calcination conditions show a substantial influence on the properties of the catalyst. Thus, for example, a lower calcination temperature of about 600° C., instead of 850° to 950° C., cannot quite be compensated by a longer calcination period of from about 4 to 8 hours, instead of 1 to 3 hours. This means that the catalyst of the process of the invention is characterized in a special manner both by its composition and by the method of its preparation.

The isomerization is carried out according to the process of the invention at a temperature of from 250° to 500° C., preferably at 300° to 450° C.

The isomerization of the invention is effected in one of the apparatuses that are common for catalytic reactions. To carry out the process, the 5,5-dimethyl dioxans may be passed discontinuously by themselves or diluted with an inert gas, such as nitrogen or a noble gas, over the catalyst present in a reactor. However, other common embodiments of a reaction with a heterogeneous catalyst, for example in the fluidized bed or in the liquid phase under pressure with a finely suspended catalyst, are also well suitable.

The reaction products may be separated by distillation, and in the case of incomplete conversion the starting material may be passed once again over the catalyst.

In this manner the process of the invention—which after all uses as starting products aldehydes and neopentyl glycol being easily obtainable—makes it possible to prepare the ethers of hydroxypivalaldehyde in good yields.

The measuring factors used in the following Examples for the 5,5-dimethyl dioxans used and the resulting ether of hydroxypivalaldehyde are defined as follows:

The conversion of the 5,5-dimethyl dioxans is the molar proportion of the reacted dioxan in percent, calculated on the amount of dioxan employed. The selectivity of the ether of hydroxypivalaldehyde is its molar proportion in percent, calculated on the reacted amount of dioxan. The product of conversion and selectivity gives the yield of ether of hydroxypivalaldehyde. All three measuring factors are indicated in molar %.

The ethers of hydroxypivalaldehyde may be easily converted into ethers of hydroxypivalic acid by way of an oxidation with oxygen in the presence of a cobalt catalyst at room temperature in the liquid phase. The tert.-butyl-peroxyesters of the ethers of hydroxypivalic acid may in their turn be obtained via the acid chloride which is reacted with tert.-butyl hydroperoxide.

The tert.-butyl-peroxyesters of the ethers of hydroxypivalic acid are especially appropriate as initiators for the polymerization of vinyl chloride or ethylene. They have in fact the same activity as the polymerization initiator tert.-butyl perpivalate (=tert.-butyl peroxyester of pivalic acid) which is common in industry, but are less volatile due to the higher polarity and the higher molecular weight. Thus, for example, 0.05% by weight of the tert.-butyl peroxyester of i-butoxypivalic acid polymerize up to 80% of vinyl chloride in 8 hours at 60° C. With the combination of 0.05% by weight of tert.-butyl per-i-butoxypivalate and 0.1% by weight of dilauroyl peroxide, the polyvinyl chloride proportion rises to more than 90% under the same conditions otherwise.

With the ethylene polymerization in a stirring vessel, one passage at 120° to 180° C. and 1800 to 3000 bar and a residence time of 60 seconds yields a conversion of about 10%; at 150° C. the conversion rate is 15%. For 1 ton of polyethylene, about 3 to 5 kg of initiator are required.

A combination of tert.-butyl peroxyesters of ethers of hydroxypivalic acid and tert.-butyl peroctoate and/or tert. butyl perbenzoate is particularly advantageous for the ethylene polymerization.

The following Examples serve to illustrate the invention.

EXAMPLE 1 AND COMPARATIVE EXAMPLES 1 AND 2

(Preparation of $C_6H_5CH_2OCH_2C(CH_3)_2CHO$ = benzyl ether of hydroxypivalaldehyde)

100 Milliliters (=51 g) of a silicon dioxide carrier in the form of silica gel having a surface of 120 m$^2$/g, an average pore radius of 150 Å and a content of 0.6% by weight of potassium and sodium are impregnated with a mixture of an acetic acid solution of 2.55 g of didymium oxide (7.63 mmols) and an aqueous solution of 2.66 g of potassium acetate (27.12 mmols), then dried and calcined for 4 hours at 600° C.

The control catalyst for Comparative Example 1 consists only of 100 ml of the SiO$_2$ carrier used above. For Comparative Example 2, 100 ml of the same SiO$_2$ carrier are impregnated with 1.52 g of potassium hydroxide (27.12 mmols) in an aqueous solution and dried. Both control catalysts are then calcined for 4 hours at 600° C.

10 Grams of 2-phenyl-5,5-dimethyl-1,3-dioxan (PDD) are passed per hour over 100 ml each of these three catalysts in a tubular reactor being heated electrically, in the temperature range of from 250° to 350° C. The reaction product benzyloxypivalaldehyde BPA is collected like the unreacted 2-phenyl-5,5-dimethyl-1,3-dioxan in cooling traps and analyzed by way of gas chromatography. The results have been summarized in the following Table. In this Table,
C$_1$ stands for Comparative Example 1.
C$_2$ stands for Comparative Example 2.

EXAMPLE 2

(Preparation of $CH_3OCH_2C(CH_3)_2CHO$ = methoxypivalaldehyde)

4.1 Grams of Di$_2$O$_3$ (12.28 mmols) are reacted under reflux with 1 ml of H$_2$O$_2$ in 55 ml of acetic acid and combined with a solution of 2.08 g of lithium hydroxide in 9 ml of H$_2$O. 16 ml = 82 g of silicon dioxide (90% by weight of SiO$_2$, 6% by weight of Al$_2$O$_3$, 4% by weight of oxides of Ti, Mg, Fe and Ca; 180 m$^2$/g of BET surface; grain size of 0.5 to 1.5 mm) are impregnated with this mixture, predried and calcined for 2 hours at 900° C. The finished catalyst contains 5% by weight of didymium oxide and 1.59% by weight of lithium oxide (43.33 mmols).

15 ml/h of 5,5-dimethyl-1,3-dioxan are passed over this catalyst at 370° C. With a conversion of 58.8 molar % of the 5,5-dimethyl-1,3-dioxan the selectivity reaches 86.2 molar % for methoxypivalaldehyde, i.e. the yield of the latter is 50.7 molar %.

COMPARATIVE EXAMPLE 3

The experiment is carried out in the same manner as has been described for Example 2, with the only exception that a commercial pumice is used as catalyst. The yield of methoxypivalaldehyde is 27.1 molar %.

EXAMPLE 3

(Preparation of $n\text{-}C_8H_{17}OCH_2C(CH_3)_2CHO$ = n-octyloxypivalaldehyde)

160 Milliliters (=82 g) of SiO$_2$ (for characteristics cf. Example 2) are impregnated with the mixture of a solution of 0.96 g of aluminum hydroxide (12.31 mmols) in 55 ml of acetic acid and 1 ml of 30% H$_2$O$_2$ and a solution of 7.15 g of sodium acetate (87.2 mmols) in 9 ml of H$_2$O, then dried in a vacuum drying cabinet and calcined for 4 hours at 600° C. 15 Milliliters (=13 g=60.8 mmols) of 2-n-heptyl-5,5-dimethyl-1,3-dioxan and about 4.5 l/h of N$_2$ are passed per hour over this catalyst in a reactor heated electrically, at a reaction temperature of 300° C.

The reaction product is collected in a cooling trap and analyzed by gas chromatography. A conversion of 37.3 molar % of the 1,3-dioxan is obtained; the selectivity to n-octyloxy-pivalaldehyde is practically 100%.

EXAMPLES 4 TO 6 AND COMPARATIVE EXAMPLES 4

(Influence of the calcination temperature on the preparation of $i\text{-}C_4H_9OCH_2C(CH_3)_2CHO$)

For preparing the precatalyst, 4.1 g of didymium oxide (12.28 mmols) are dissolved under reflux in 55 ml of acetic acid and 1 ml of 30% H$_2$O$_2$. Thereafter 8.55 g of potassium acetate (87.16 mmols) in 9 ml of H$_2$O are added. 160 ml (=82 g) of SiO$_2$ (for characteristics cf. Example 2) are impregnated with this mixture and dried in the vacuum drying cabinet at 100° C. This precatalyst is then calcined at different temperatures and for different periods of time, as may be seen from the following Table:

| Catalyst Number | Period of calcination in hours | Calcination temperature in °C. |
|---|---|---|
| 1 | 8 | 600 |
| 2 | 2 | 900 |
| 3 | 4 | 900 |

15 ml/h (=13.5 g/h=85.5 mmols/h) of 2-isopropyl-5,5-dimethyl-1,3-dioxan are passed over 160 ml each of the K$_2$O/Di$_2$O$_3$/SiO$_2$ catalyst 1, 2, 3 thus prepared and for reasons of comparison also over a catalyst of pumice (grain size 2 to 6 mm), at temperatures having been

| No. | Temp. (°C.) | Catalyst Di$_2$O$_3$ (mmols) | K$_2$O (mmols) | K$_2$O precursor | Conversion PDD (molar-%) | Selectivity BPA (molar-%) | Yield BPA (molar-%) |
|---|---|---|---|---|---|---|---|
| C$_1$ | 250 | — | — | — | 100 | — | — |
| C$_2$ | 300 | — | 27.1 | KOH | 27 | 97 | 26 |
| C$_2$ | 350 | — | 27.1 | KOH | 55 | 62 | 34 |
| 1 | 300 | 7.63 | 27.1 | KOAc | 87 | 100 | 87 |
| 1 | 325 | 7.63 | 27.1 | KOAc | 95 | 92 | 87 | increased stepwise (300° C. for 7 hours, 350° C. for 7 to 8 hours and 370° C. for 7 to 8 hours), in a device as has been described in Example 1. 4 l/h (relative to 0° C., 1 bar) of nitrogen are passed over the catalyst together with the 1,3-dioxan derivative. The results at 350° C.—at this temperature an optimum formation of i-butoxypivalaldehyde is observed—have been summarized in the following Table and compared with the result when using pumice as catalyst. The conversion and selectivity values are determined by way of gas chromatography.

| Example | Catalyst Number | 1,3-dioxan conversion (molar-%) | i-butoxypivalaldehyde selectiv. (molar-%) | yield (molar-%) |
|---|---|---|---|---|
| 4 | 1 | 76.5 | 68.3 | 52.2 |
| 5 | 2 | 88.5 | 96.7 | 85.7 |
| 6 | 3 | 90.2 | 57.5 | 52.1 |
| C₄ | pumice | 34.7 | 80.0 | 30.0 |

C₄ = Comparative Example 4

The reaction products obtained with catalyst No. 2 in Example 5 are collected over a prolonged period of time and distilled over a fractionating column having a length of 2.4 m and being charged with saddles of nets of stainless steel at 40 mbar. After a small amount of first runnings had passed over, the unreacted 5,5-dimethyl-1,3-dioxan derivative is first separated at about 70° C., and at about 80° C. the i-butoxypivalaldehyde is then distilled off as a substance which is pure according to the analysis by gas chromatography. A small higher boiling residue (boiling point$_{30}$ > 83° C.) does not contain any more aldehyde.

What is claimed is:

1. A process for the preparation of an ether of hydroxypivalaldehyde of the formula $RCH_2OCH_2-C(CH_3)_2CHO$ wherein R is hydrogen, linear or branched alkyl having from 1 to 7 carbon atoms, cyclohexyl or phenyl which comprises isomerizing a 5,5-dimethyl-1,3-dioxane compound having the structure:

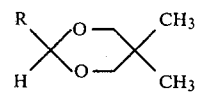

at a temperature in the range of 250° C. to 500° C. in the presence of a catalyst containing silicon dioxide, 4 to 40 mmols per 100 grams SiO₂ of an oxide or hydroxide of didymium and 10 to 100 mmols per 100 grams of SiO₂ of an oxide or hydroxide of sodium or potassium, or both, said catalyst being formed by calcination at a temperature of from 600° C. to 1000° C. for 30 minutes to 8 hours.

2. The process of claim 1 wherein the isomerization is conducted at a temperature in the range of 300° C. to 450° C.

3. The process of claim 1 wherein the calcination is conducted at a temperature in the range of 850° C. to 950° C. for 1 to 4 hours.

* * * * *